US012287437B2

United States Patent
Riehl et al.

(10) Patent No.: US 12,287,437 B2
(45) Date of Patent: Apr. 29, 2025

(54) QUANTITATIVE PULSE SELECTION FOR PHOTON-COUNTING COMPUTED TOMOGRAPHY SCANNING SYSTEMS

(71) Applicant: Analog Devices, Inc., Wilmington, MA (US)

(72) Inventors: Patrick S. Riehl, Lynnfield, MA (US); Sunrita Poddar, Jamaica Plain, MA (US)

(73) Assignee: ANALOG DEVICES, INC., Wilmington, MA (US)

( * ) Notice: Subject to any disclaimer, the term of this patent is extended or adjusted under 35 U.S.C. 154(b) by 112 days.

(21) Appl. No.: 18/065,045

(22) Filed: Dec. 13, 2022

(65) Prior Publication Data
US 2023/0228888 A1    Jul. 20, 2023

Related U.S. Application Data

(60) Provisional application No. 63/300,953, filed on Jan. 19, 2022.

(51) Int. Cl.
*G01T 1/17* (2006.01)
*A61B 6/03* (2006.01)
*A61B 6/42* (2024.01)

(52) U.S. Cl.
CPC ............. *G01T 1/17* (2013.01); *A61B 6/032* (2013.01); *A61B 6/4241* (2013.01)

(58) Field of Classification Search
CPC ......... G01T 1/17; G01T 1/2985; G01T 1/247; A61B 6/032; A61B 6/4241; A61B 6/54; A61B 6/58
See application file for complete search history.

(56) References Cited

U.S. PATENT DOCUMENTS

| 7,180,074 B1 | 2/2007 | Crosetto |
| 7,800,070 B2 | 9/2010 | Weinberg et al. |
| 9,645,260 B2 | 5/2017 | Abraham et al. |
| 9,750,471 B2 | 9/2017 | Schirra et al. |

(Continued)

FOREIGN PATENT DOCUMENTS

| JP | S6021474 A | 2/1985 |
| WO | 2013093726 A1 | 6/2013 |

OTHER PUBLICATIONS

Gustavsson et al., *A High-Rate Energy-Resolving Photon-Counting ASIC for Spectral Computed Tomography*, © 2012 IEEE Transactions on Nuclear Science, 14 pages.

*Primary Examiner* — Kiho Kim
(74) *Attorney, Agent, or Firm* — ARENTFOX SCHIFF LLP

(57) ABSTRACT

One embodiment is a method for counting charge events detected by a pixel in a photon-counting computed tomography (PCCT) scanning system comprising a plurality of discriminators, wherein each discriminator is associated with a respective one of a plurality of threshold voltage levels. The method includes detecting a signal output from one of the discriminators; incrementing a quantitative count corresponding to the threshold voltage level associated with the one of the discriminators if the detected discriminator output signal meets a first condition; and incrementing a qualitative count if the detected discriminator output signal meets at least one second condition.

20 Claims, 16 Drawing Sheets

(56) References Cited

U.S. PATENT DOCUMENTS

| | | |
|---|---|---|
| 10,080,533 B2 | 9/2018 | Roessl et al. |
| 10,768,318 B2 | 9/2020 | Qiang et al. |
| 2010/0181491 A1 | 7/2010 | Karim et al. |
| 2015/0063527 A1 | 3/2015 | Daerr et al. |
| 2016/0377745 A1 | 12/2016 | Daerr et al. |
| 2017/0205284 A1 | 7/2017 | De Geronimo |
| 2020/0379133 A1 | 12/2020 | Burr et al. |
| 2020/0393576 A1* | 12/2020 | Harris .................. G01T 1/171 |
| 2021/0239856 A1 | 8/2021 | Sjolin |

* cited by examiner

QUANTITATIVE PULSE SELECTION FOR PHOTON-COUNTING COMPUTED TOMOGRAPHY SCANNING SYSTEMS

CROSS-REFERENCE TO RELATED APPLICATION

This application claims the benefit of and hereby incorporates by reference, for all purposes, the entirety of the contents of U.S. Provisional Application No. 63/300,953, filed Jan. 19, 2022, entitled, "QUANTITATIVE PULSE SELECTION FOR PHOTON-COUNTING COMPUTED TOMOGRAPHY SCANNING SYSTEMS".

FIELD OF THE DISCLOSURE

This disclosure relates generally to the field of photon-counting computed tomography (PCCT) scanning systems and, more particularly, to a quantitative pulse selection technique for use in such systems.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Figure 1:
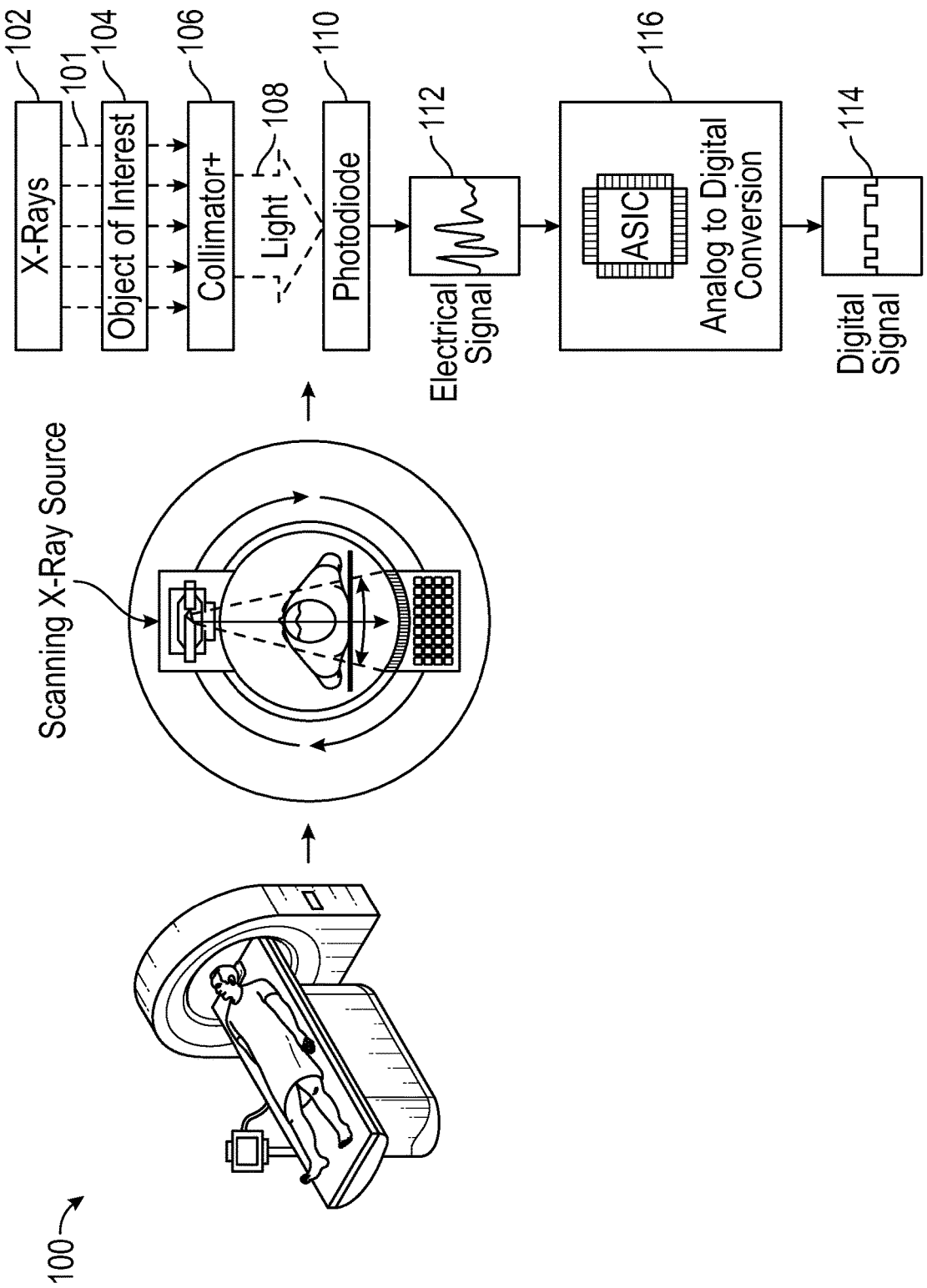
FIG. 1 is a schematic diagram illustration of operation of a conventional CT scanning system in accordance with features of certain embodiments described herein.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C). The term "between," when used with reference to measurement ranges, is inclusive of the ends of the measurement ranges. When used herein, the notation "A/B/C" means (A), (B), and/or (C).

The description uses the phrases "in an embodiment" or "in embodiments," which may each refer to one or more of the same or different embodiments. Furthermore, the terms "comprising," "including," "having," and the like, as used with respect to embodiments of the present disclosure, are synonymous. The disclosure may use perspective-based descriptions such as "above," "below," "top," "bottom," and "side"; such descriptions are used to facilitate the discussion and are not intended to restrict the application of disclosed embodiments. The accompanying drawings are not necessarily drawn to scale. Unless otherwise specified, the use of the ordinal adjectives "first," "second," and "third," etc., to describe a common object, merely indicate that different instances of like objects are being referred to and are not intended to imply that the objects so described must be in a given sequence, either temporally, spatially, in ranking or in any other manner.

In the following detailed description, reference is made to the accompanying drawings that form a part hereof, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Further, the present disclosure may repeat reference numerals and/or letters in the various examples. This repetition is for the purpose of simplicity and clarity and does not in itself dictate a relationship between the various embodiments and/or configurations discussed. Example embodiments that may be used to implement the features and functionality of this disclosure will now be described with more particular reference to the accompanying FIGURES.

Referring to FIG. 1, a traditional computed tomography (CT) scanning system 100 employs X-rays 101 generated by an X-ray source 102 and passed through an object of interest 104. The X-rays are transformed by a collimator and scintillator 106 into light 108 that is captured by a detector implemented as a photodiode arrays 110. The photodiode arrays 110 transform the light 108 into analog electrical signals 112, which are converted into digital signals 114 using an analog-to-digital (A/D) converter 116. The digital signal output from the A/D converter is used to produce a gray scale image referred to as a CT scan.

PCCT imaging may offer significant advantages and improvements over existing CT imaging techniques described above. A PCCT system employs a photon-counting detector (PCD) comprising a semiconductor layer for implementing an array of detector pixels that register the interactions of individual photons with the PCD. By tracking the deposited energy of each interaction, detector pixels of a PCD record an approximate energy spectrum as well as intensity of the photons, such that PCCT is a spectral, or energy-resolved, CT technique. In contrast, traditional CT scanners use energy-integrating detectors (EIDs) in which the total energy from one or more photons as well as electronic noise deposited in a pixel during a fixed period of time is registered. EIDs therefore register only photon intensity, analogous to black-and-white photography. In contrast, PCDs register both photon intensity and spectral information, analogous to color photography.

PCCT imaging turns the three-step process described above into a more streamlined direct conversion from X-ray to charge via semiconductor layer comprising the PCD. In particular, the semiconductor material used to implement the PCD efficiently turns each X-ray photon into a burst of charge that is proportional to the energy of the X-ray. Benefits of this technology include improved signal-to-noise, reduced X-ray dose to the patient due to the higher resolution that may be achieved with the same X-ray dose, improved spatial resolution and, through use of several "energy bins," the ability to distinguish multiple contrast agents and multiple types of materials/tissues.

When a photon interacts in a PCD, the height of a resulting electrical pulse is approximately proportional to the energy of the photon. By comparing each pulse produced in a pixel with a suitable low-energy threshold, contributions from low-energy events (resulting from both photon interactions and electronic noise) can be filtered out. As a result, PCDs have higher signal-to-noise and contrast-to-noise ratios as compared to EIDs, enabling an increase in image quality at the same X-ray exposure level or a decrease in patient X-ray dose with the same image quality.

Introduction of more energy thresholds above the low-energy threshold enables a PCD to be divided into several discrete energy bins. Each registered photon is assigned to a specific bin depending on its energy, such that each pixel measures a histogram of the incident X-ray spectrum. This spectral information enables a qualitative determination of the material composition of each pixel in the reconstructed CT image, as opposed to the estimated average linear attenuation coefficient obtained in a conventional CT scan. Additionally, using more than two energy bins enables discrimination between dense bones and calcifications versus heavier elements commonly used as contrast agents, reducing the need for a reference scan before contrast injection and thereby further reducing the amount of X-ray dose to which a patient is subjected.

Figure 2:
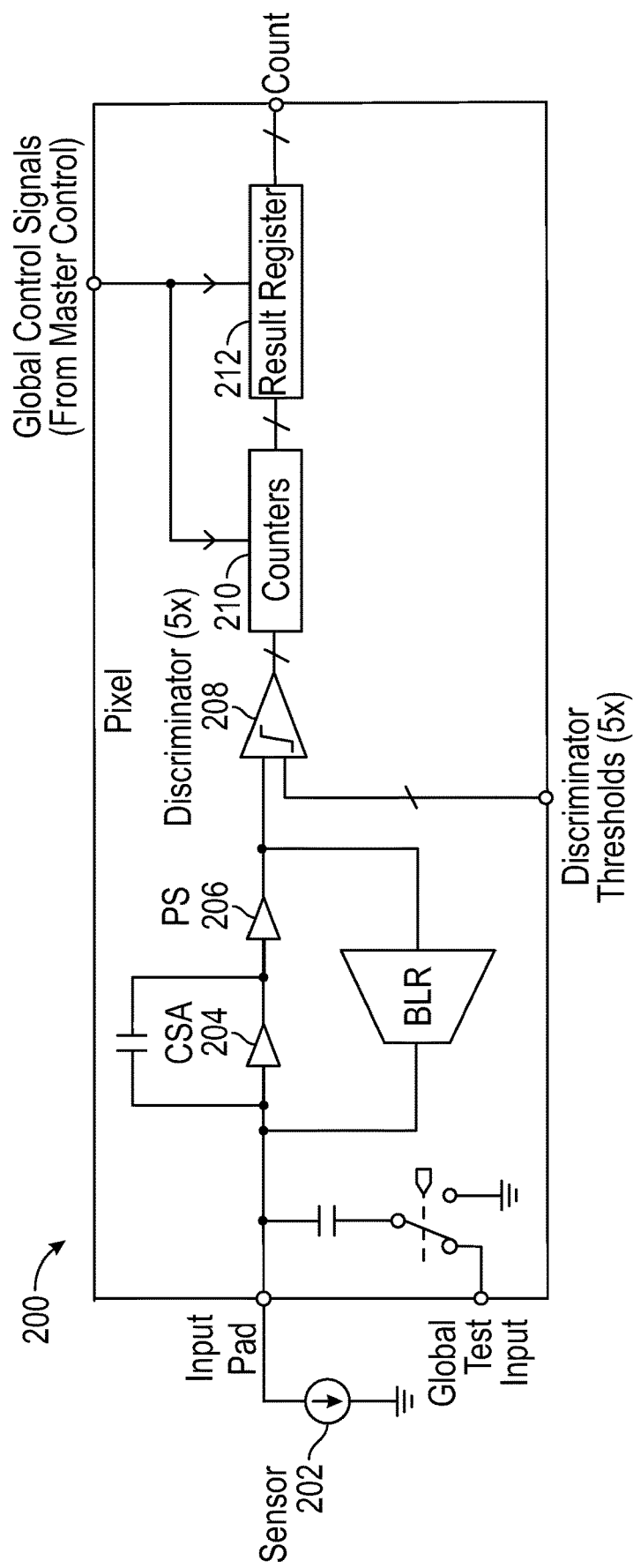
FIG. 2 is a schematic block diagram of an example signal processing architecture for a PCCT scanning system in accordance with features of certain embodiments described herein.

FIG. 2 illustrates a schematic diagram of an example signal processing architecture for a PCCT system 200 comprising a PCD including a plurality of detector pixels, represented in FIG. 2 by a single pixel. In operation, a pulse of current comes in from a sensor 202, is amplified by a charge-sensitive amplifier (CSA) 204 and shaped by a pulse shaper (PS) 206. The voltage pulse output from the PS 206 is input to a set of N discriminators (or comparators) 208, which respectively compare the pulse to N increasing voltage thresholds. The set of discriminators 208 create pulsed digital outputs in a "thermometer code." The pulses may be counted at each level, or threshold, by counters 210, with the resulting count values (which may be temporarily stored in result registers 212) representing how many X-ray hits at each of the N thresholds have occurred. It will be recognized that the thresholds are set to match the different voltages corresponding to the different energy photons. In accordance with features of embodiments described herein, in addition to a quantitative counter corresponding to each of the N thresholds, the counters 210 include a qualitative counter for purposes to be described in greater detail below.

Figure 3:
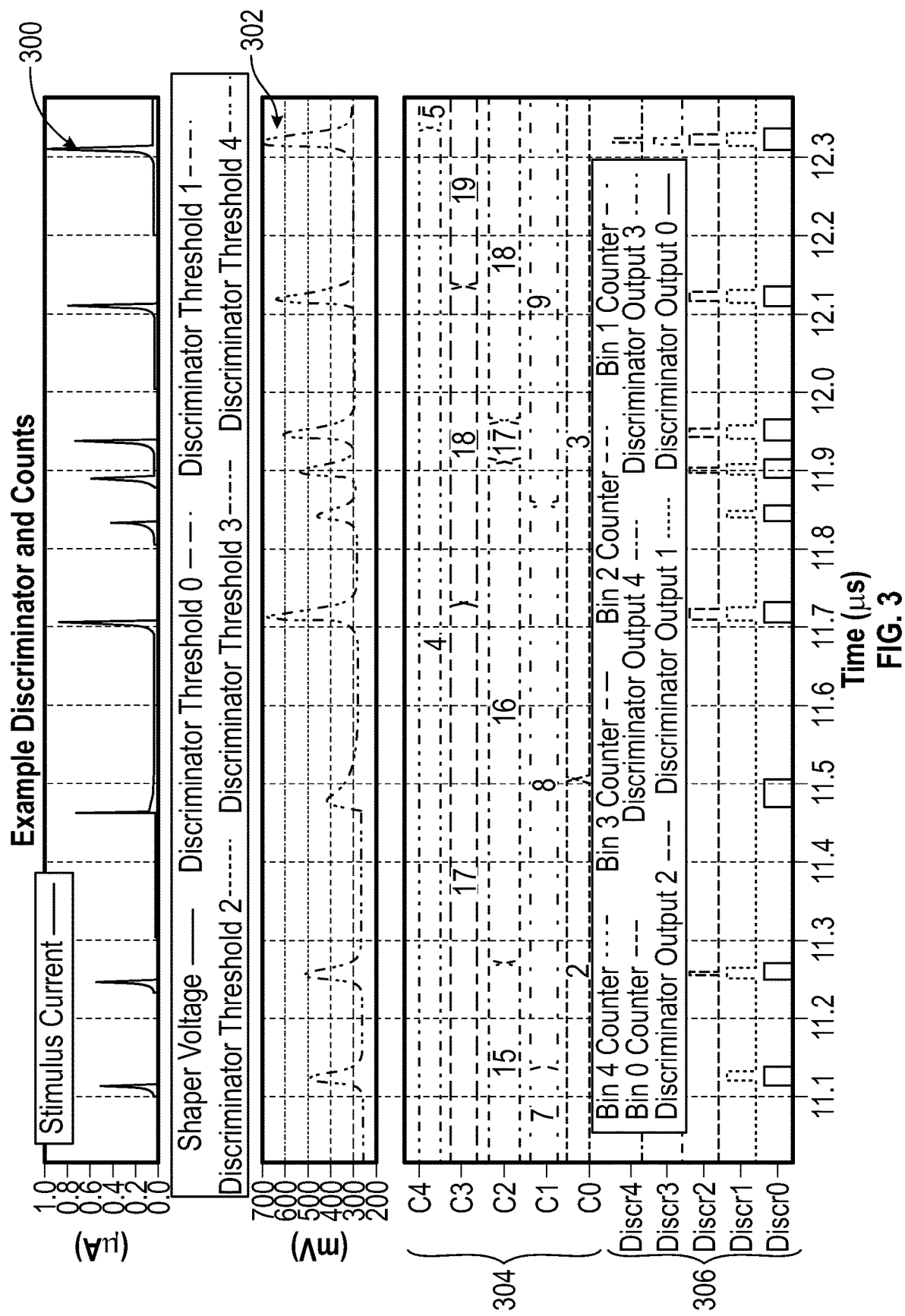
FIG. 3 is a graph illustrating results of a simulation example of the PCCT scanning system of FIG. 2 in accordance with features of certain embodiments described herein.

FIG. 3 is a graph illustrating results of a simulation example of a PCCT system illustrated in FIG. 2 in which there are no overlapping charge events. A first waveform 300 represents a stimulus current from the sensor 202 and a second waveform 302 represents the corresponding shaper voltage from the PS 206 vs. increasing voltage discriminator threshold voltages (vth[0]–vth[4]) expressed in millivolts (mV). Waveforms 304 represent the corresponding pulses counted at each level by counters 210. Finally, waveforms 306 represent outputs of discriminators 208 input to counters 210. It will be noted from FIG. 3 that, for each pulse of current, a voltage pulse from the pulse shaper generates outputs on the discriminators 208. Counting by the counters 210 of the peak discriminator output for each pulse is the desired response.

When all of the pulses occur far enough apart in time, there are multiple ways to effectively implement counters to count and "bin" the pulses. Two common techniques of doing so include asynchronous edge (asynch_edge) counting and peak zero (peak_zero) counting.

Using asynchronous edge counting, an asynchronous counter is associated with each discriminator output. As a result, the counter increments for any energy level above the threshold level of the associated discriminator. If a "binned" value is required, for each counter, the counts of the higher threshold level counters must be subtracted from the count to determine the correct count for threshold level. For example, the counter associated with discriminator 0 is also incremented for every discriminator 1-N count; therefore, to get an accurate level 0 count, counts for discriminators 1–N must be subtracted from the count for discriminator 0.

Similarly, the counter associated with discriminator 1 is also incremented for every discriminator 2–N count; therefore, to get an accurate level 1 count, counts for discriminators 2–N must be subtracted from the count for discriminator 1.

Using peak zero counting, the edges of the signals output from discriminator 0 are used to decide which counter to increment. The method is basically to increment only the maximum discriminators count that occurs between the rise and fall of discriminator 0.

Both asynchronous edge counting and peak zero counting work reasonably well when the events being counted are spaced apart without any overlap. If there are no other charge events, there will always be an orderly sequence starting and ending with discriminator 0 rising and falling. There will also be a rising edge of all levels below the maximum switching discriminator.

Figure 4A:
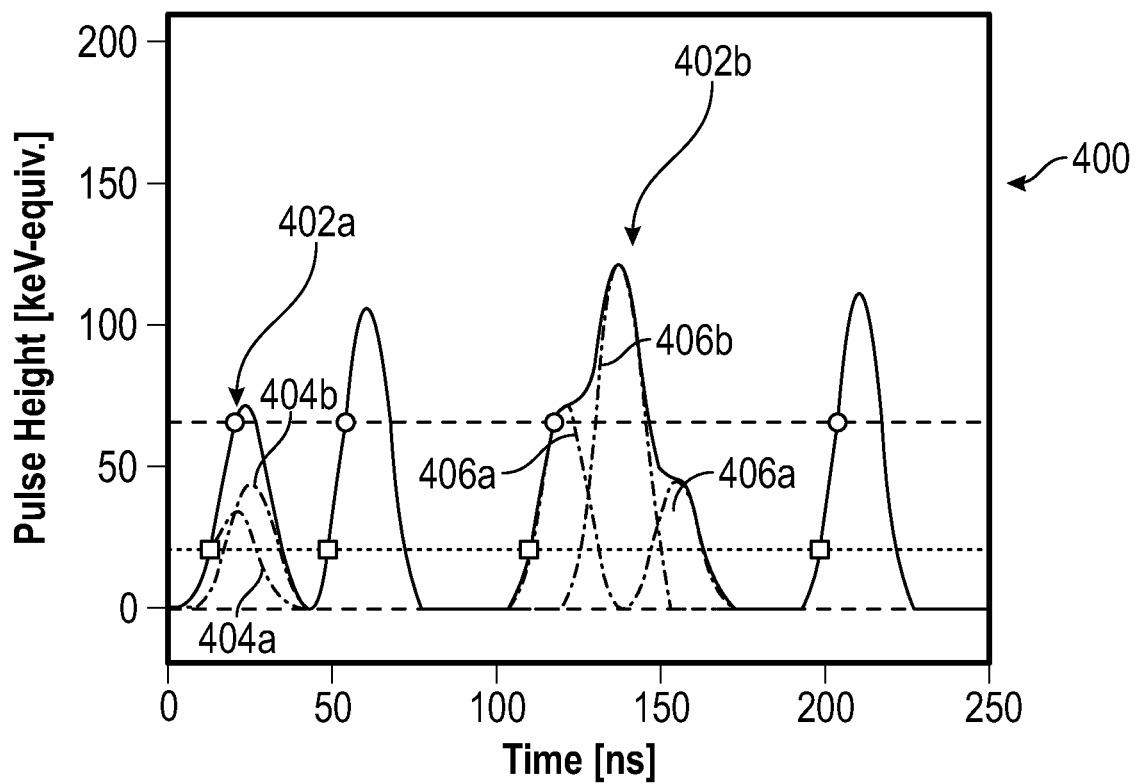
FIG. 4A illustrates an example of charge event pileup in accordance with features of certain embodiments described herein.

In reality, charge events may occur too close together in time to be distinguished from one another, which may result in multiple charge events being counted as a single charge event with incorrect energy. This phenomenon is typically referred to as "pileup," an example of which is illustrated in FIG. 4A. Referring to FIG. 4A, a graph 400 illustrates two instances of pileup, designated by reference numerals 402a and 402b. In particular, the instance 402a corresponds to a pileup of two overlapping charge events 404a and 404b. The instance 402b corresponds to a pileup of three overlapping charge events 406a-406c.

Figure 4B:
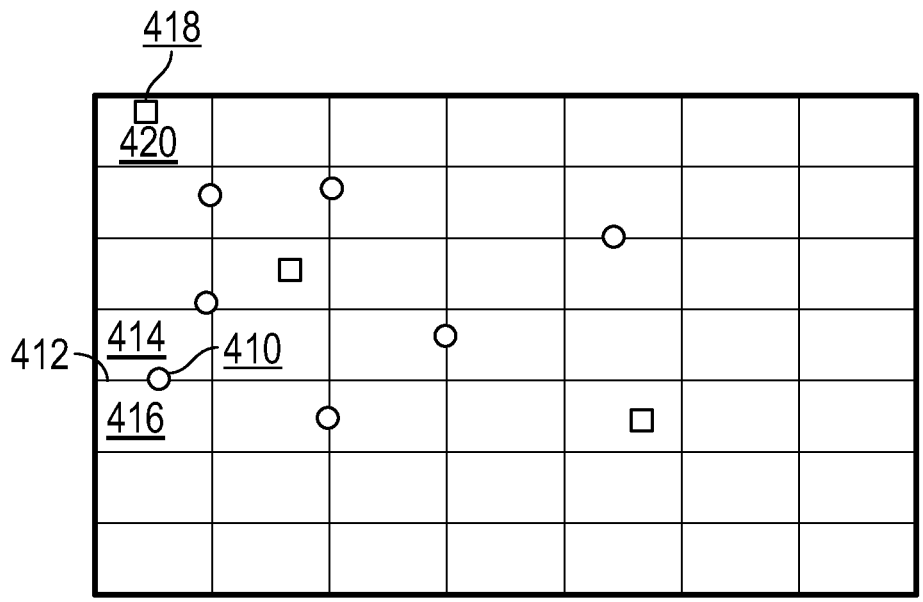
FIG. 4B illustrates examples of charge sharing in accordance with features of embodiments described herein.

Additionally, a charge event may occur on a boundary between neighboring pixels, resulting in the charge energy being split between (or among) the pixels. This phenomenon is typically referred to as "charge sharing," an example of which is illustrated in FIG. 4B. Referring to FIG. 4B, a charge event 410 occurs on a boundary 412 between pixels 414, 416, resulting in charge sharing between those pixels. In contrast, a charge event 418 occurs completely within the boundaries of a pixel 420.

Both pileup and charge sharing can cause an error when measuring the photon energy. Over the course of a measurement frame, some events may suffer from pileup and/or charge sharing while others may not.

Various charge event counting techniques have been proposed and implemented. For example, a technique referred to herein as a "tickdown" counter employs an asynchronous state machine to count "down-tick" events to maximize the likelihood of matching the total event count. Another method that has been employed is referred to as a ToT technique, in which if a spectral threshold is exceeded for a period of time longer than expected for a single event, an event at that threshold is immediately counted and the timer is reset. The ToT technique provides an improvement in counting performance especially at high flux. A method to reduce the effects of charge sharing may be referred to as a "coincidence counter" method, which attempts to correct individual events for the effects of charge sharing.

In accordance with features of embodiments described herein for implementing a QPS system, if incidents of pileup and/or charge sharing can be detected, the corresponding charge events can be tallied by a qualitative counter, the purpose of which is to maintain an accurate record of total counts. Only the events that do not measurably suffer from pileup and/or charge sharing are binned by the energy-sensitive quantitative detectors. As long as a statistically significant number of qualitative events can be measured during the measurement frame, the overall energy spectrum can be estimated without systematic errors resulting from charge sharing and pileup. In certain embodiments, QPS techniques are combined with ToT techniques for improved performance. Unlike the coincidence counter method, in the QPS method described herein, charge sharing is detected and corresponding events are disregarded for the purpose of estimating energy spectrum.

Figure 5A:
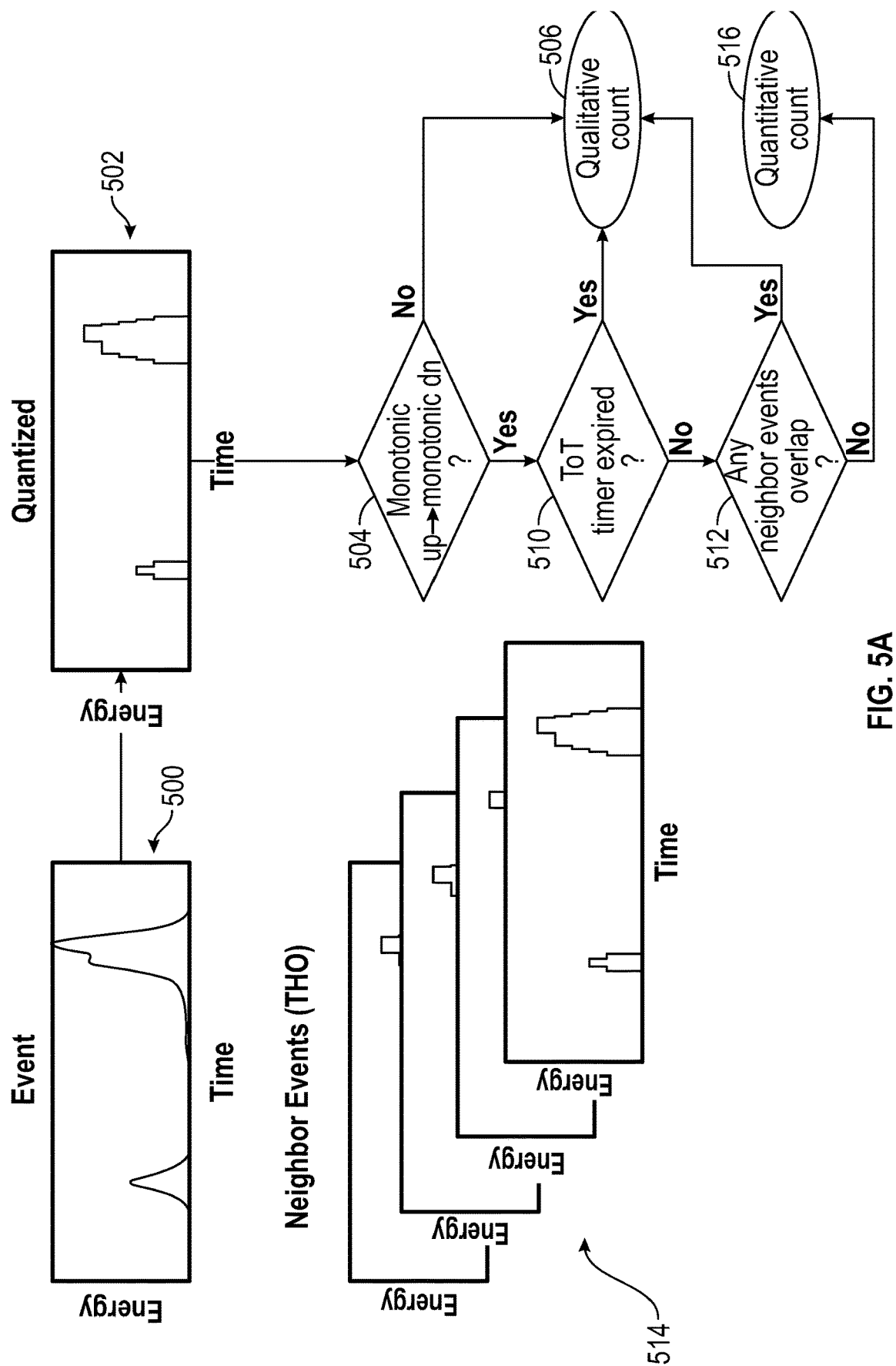
FIG. 5A is a flowchart illustrating operation of a quantitative pulse selection (QPS) technique in accordance with features of embodiments described herein.

FIG. 5A is a flowchart illustrating example operation of one embodiment of a QPS system. As shown in FIG. 5A, an event detected at a pixel (step 500) is quantized (step 502) and then in step 504, a determination is made whether the quantized event exhibits monotonic up and down characteristics, indicating that the detected event is not affected by pileup. Specifically, this condition is met if and only if the quantized event is solely composed of a series of low-to-high transitions starting from the baseline level followed by a series of high-to-low transitions terminating at the baseline level. If not (indicating that the detected charge event is affected by pileup), in step 506, the event is counted by a qualitative counter; otherwise, in step 510, a determination is made whether a ToT parameter has been exceeded. If the ToT parameter has been exceeded, the event is (or, depending on the amount of time by which the ToT parameter has been exceeded, events are) counted by the qualitative counter in step 506; otherwise, in step 512, a determination is made whether an overlapping event has been detected by any neighboring pixels 514, which indicates a charge sharing situation. If it is determined that an overlapping event has been detected by one or more neighboring pixels 516, the event is counted by the qualitative counter in step 506; otherwise, the event is binned by the quantitative counters in step 516.

Figure 5B:
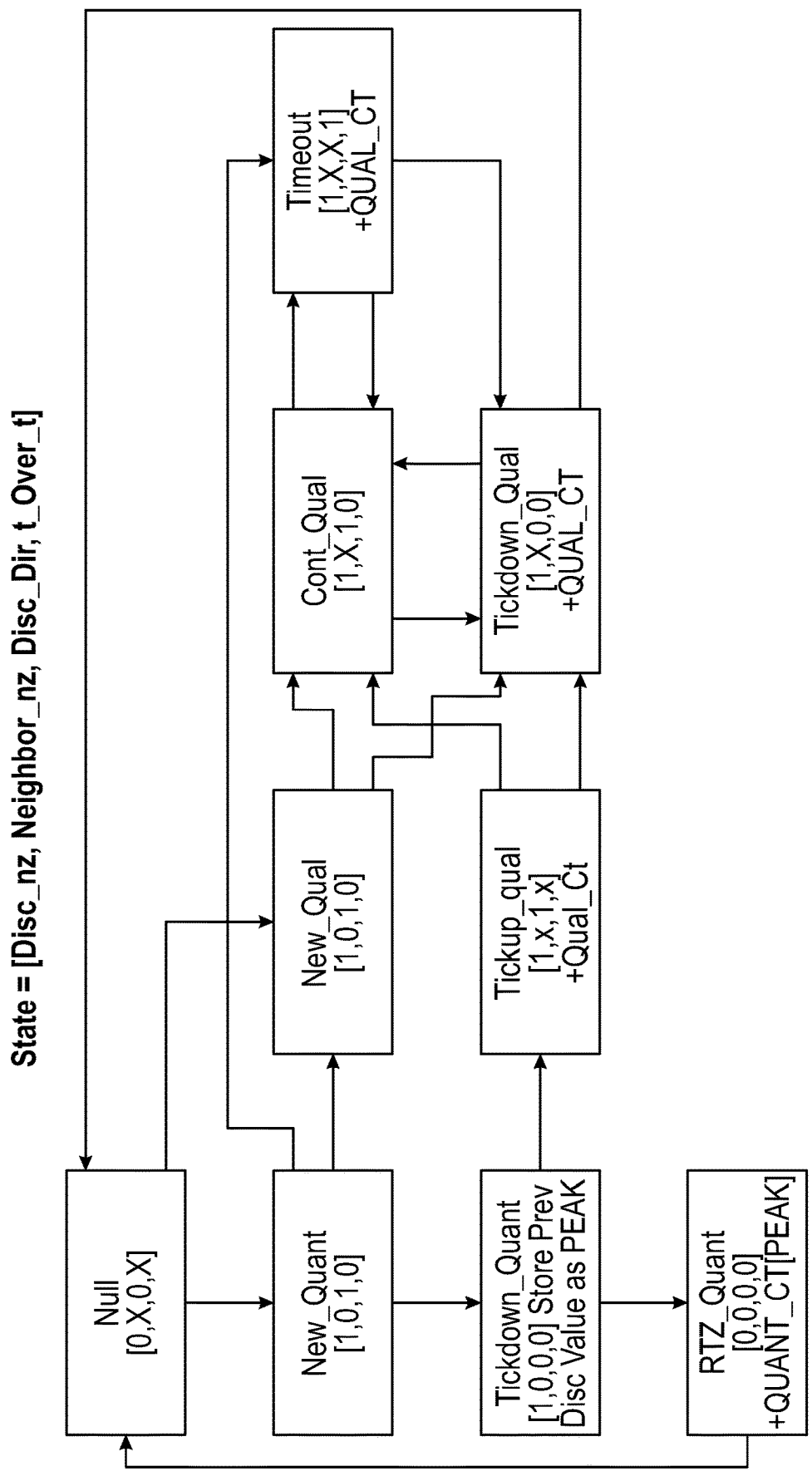
FIG. 5B is a state machine implemented by a QPS technique in accordance with features of embodiments described herein.

FIG. 5B is a state machine illustrating example operation of a QPS system in accordance with embodiments described herein. State variables for the state machine of FIG. 5B are defined as follows:

disc_nz: Discriminator output is non-zero (aka disc_out[0])

neighbor_nz: At least one neighbor (N,S,E,W) discriminator output is non-zero OR of all neighbors' disc_nz disc_dir: Discriminator output last direction
    0→last disc output was higher
    1→last disc output was lower t_over_t: Time-over-threshold indicator
    0→default
    1→time-over-threshold timer has expired Outputs for the state machine of FIG. 5B are defined as follows:

+QUAL_CT: Increment qualitative pulse counter

+QUANT_CT[N]: Increment quantitative pulse counter of bin N

After a counter is incremented, t_over_t is reset to zero. It should be noted that more internal state variables than defined above may be required to keep track of state history.

Figure 6A:
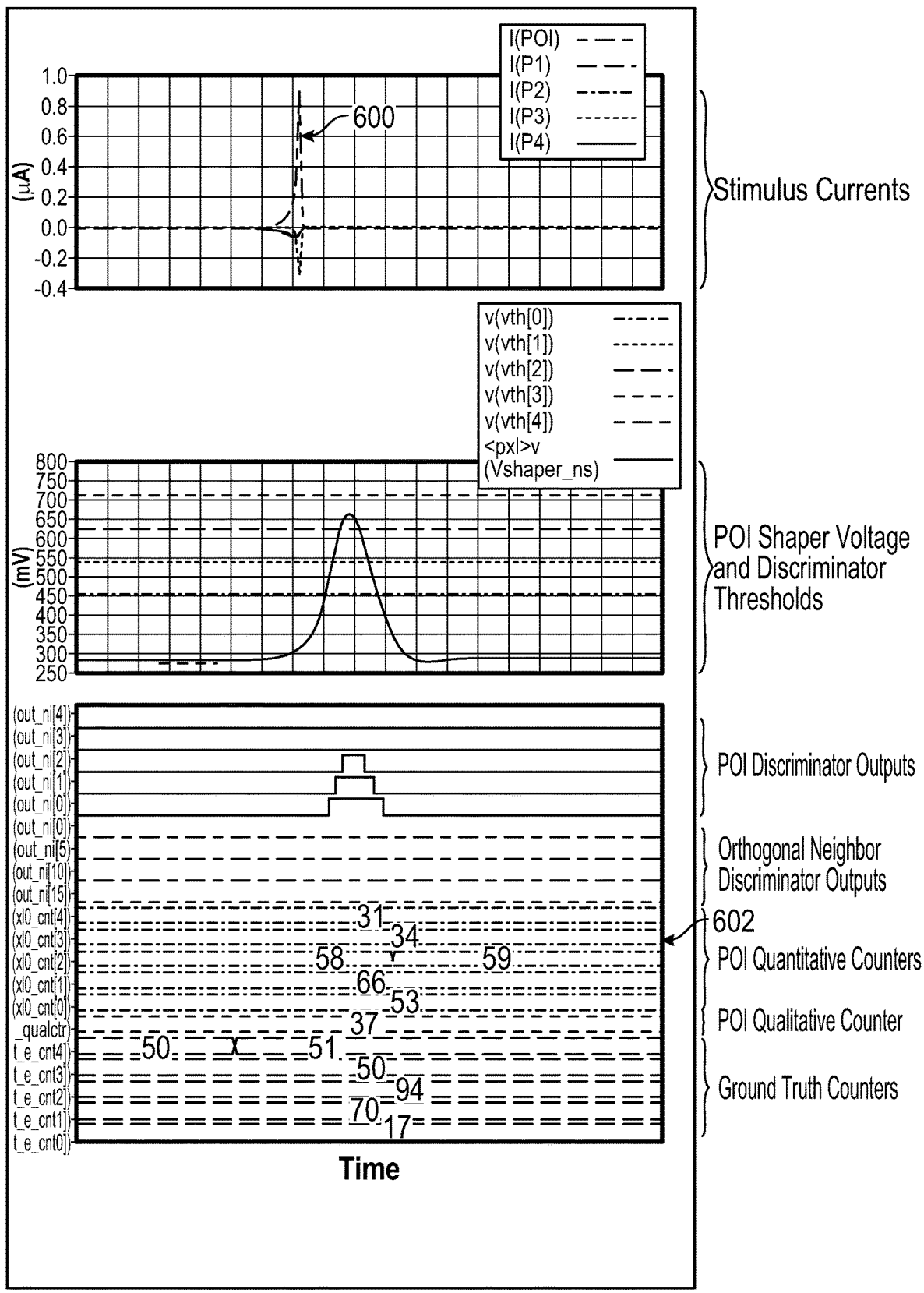
FIGS. 6A-6C illustrate counting of charge events detected at a pixel-of-interest (POI) in accordance with features of embodiments described herein.

FIG. 6A illustrates counting of an event 600 detected at a POI in accordance with features of embodiments described herein for implementing a QPS counting method. As shown in FIG. 6A, the event 600 is not affected by pileup (i.e., POI discriminator output waveforms are monotonic up and down and ToT is not exceeded) or charge sharing (no activity on waveforms corresponding to orthogonal neighbor discriminator outputs); therefore, the event 600 is counted by a quantitative counter corresponding to bin 2 (represented by a waveform 602).

Figure 6B:
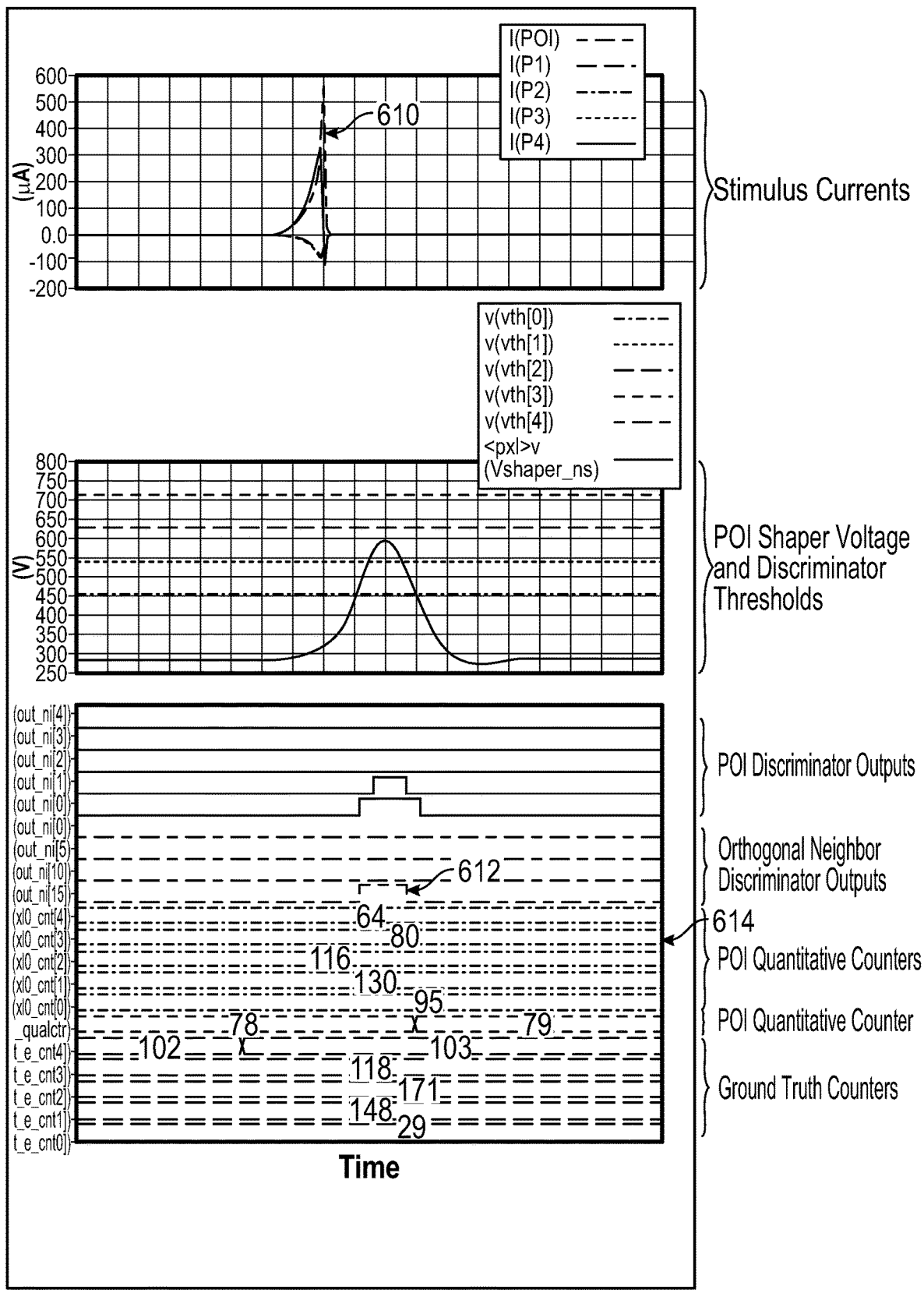

FIG. 6B illustrates counting of an event 610 detected at a POI in accordance with features of embodiments described herein for implementing a QPS counting method. As shown in FIG. 6B, the event 610 is not affected by pileup (i.e., POI discriminator output waveforms are monotonic up and down and ToT is not exceeded); however, the event 610 is affected by or charge sharing, as indicated by activity on at least one of the waveforms corresponding to orthogonal neighbor discriminator outputs (i.e., waveform 612). As a result, the event 610 is counted by the qualitative counter (represented by a waveform 614).

Figure 6C:
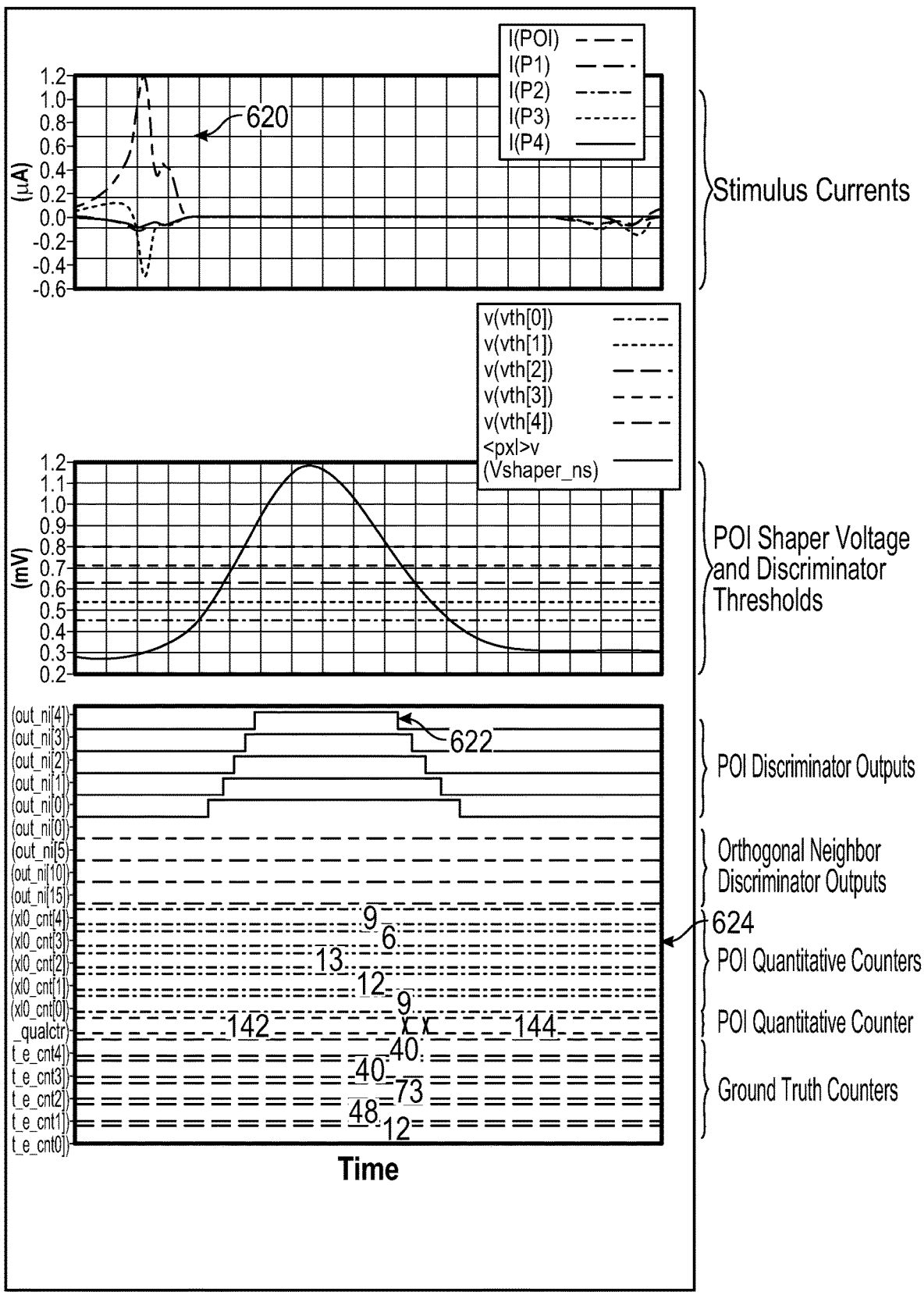
Figure 7A:
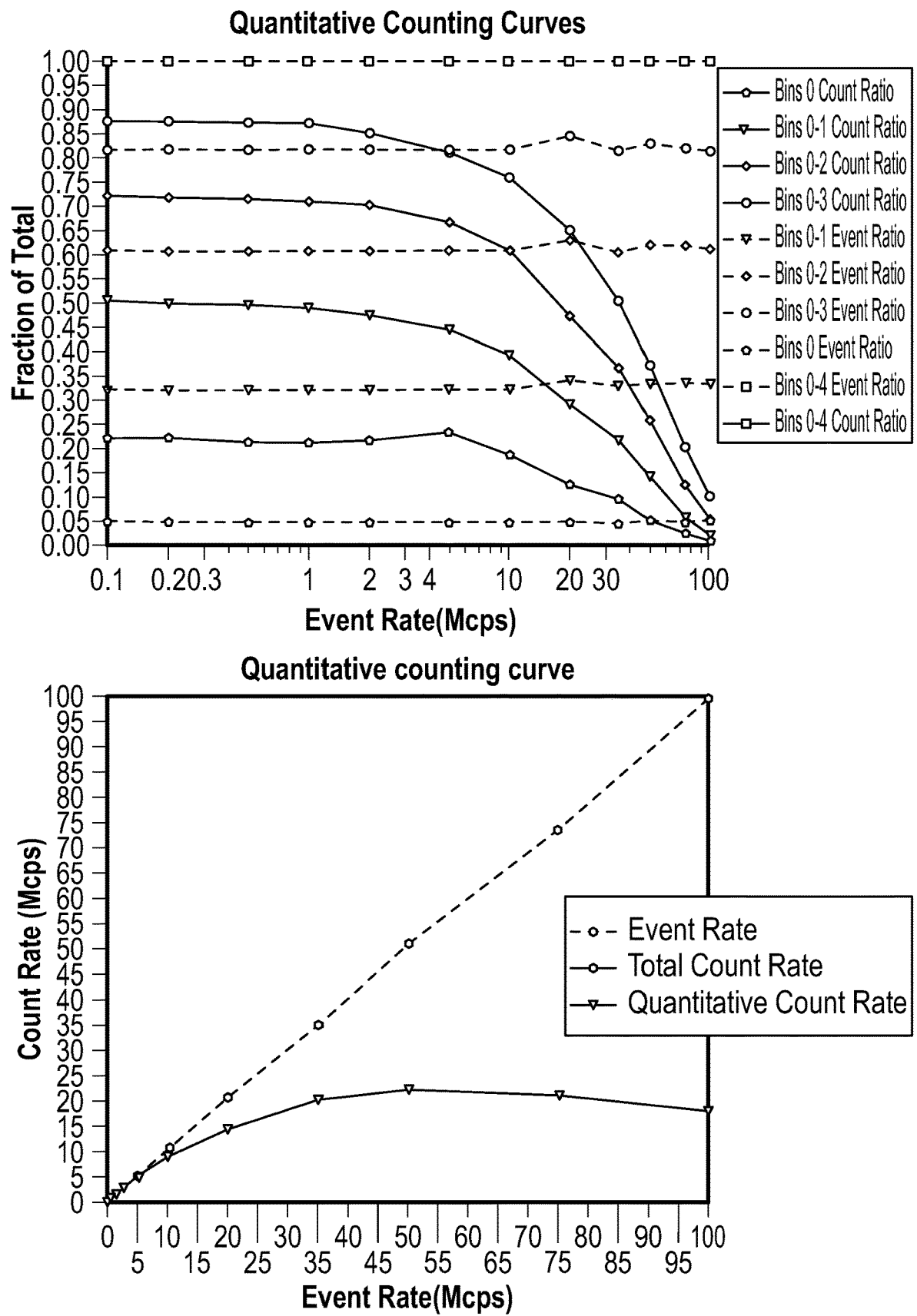
FIGS. 7A-7D illustrate quantitative counting curves and qualitative counting curves for a variety of PCCT counting methods as compared to ground truth in accordance with features of embodiments described herein.
Figure 7B:
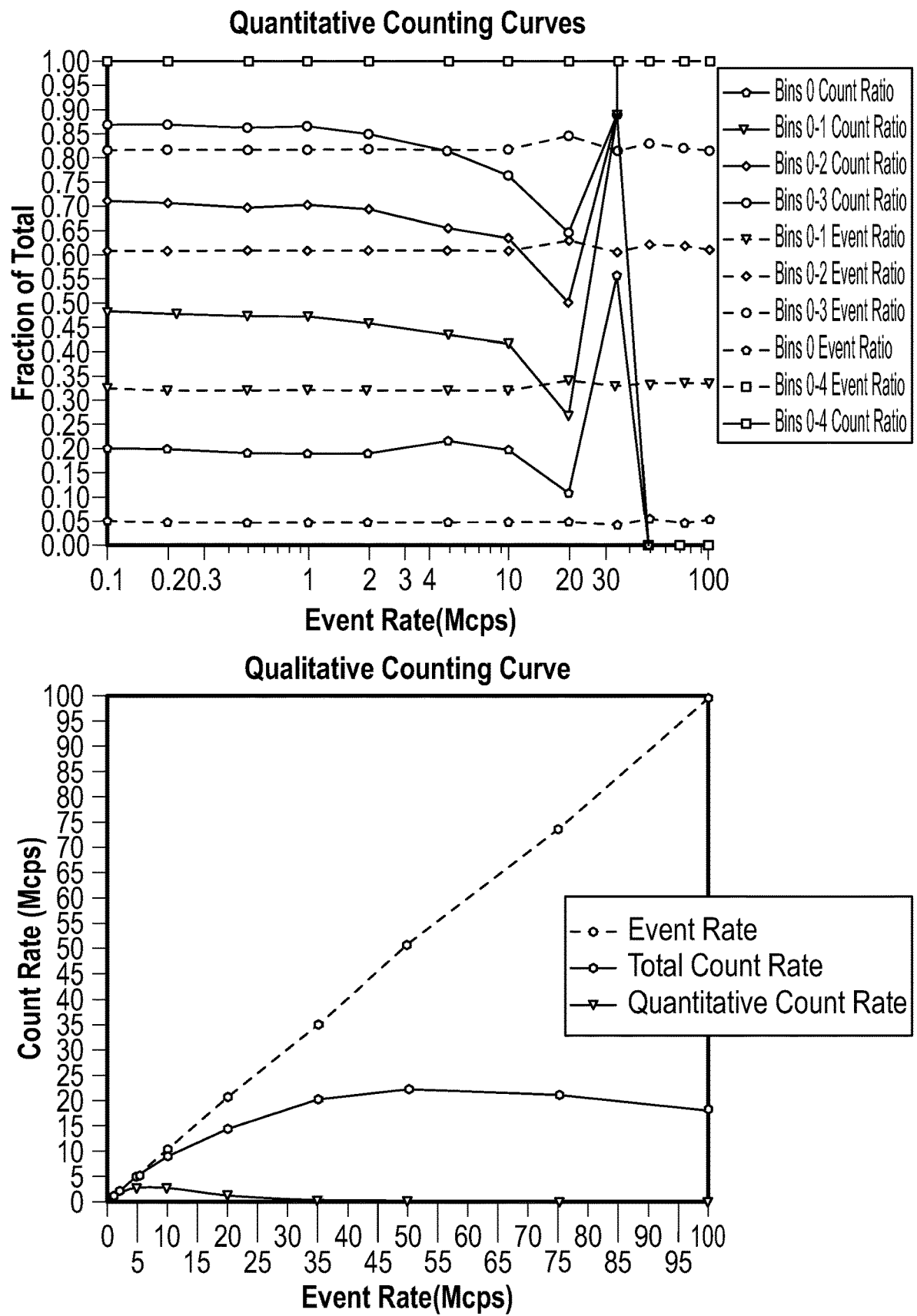
Figure 7C:
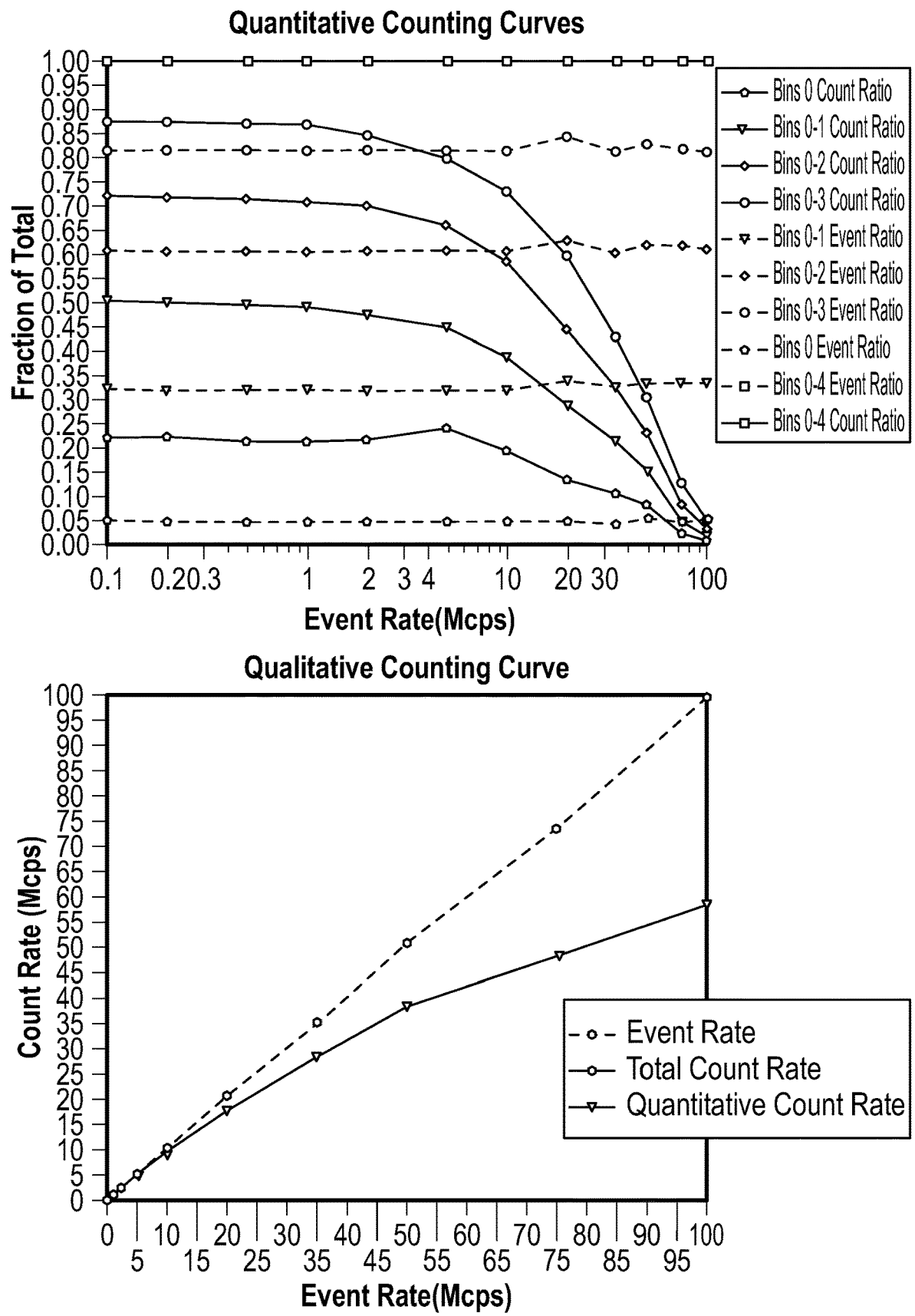
Figure 7D:
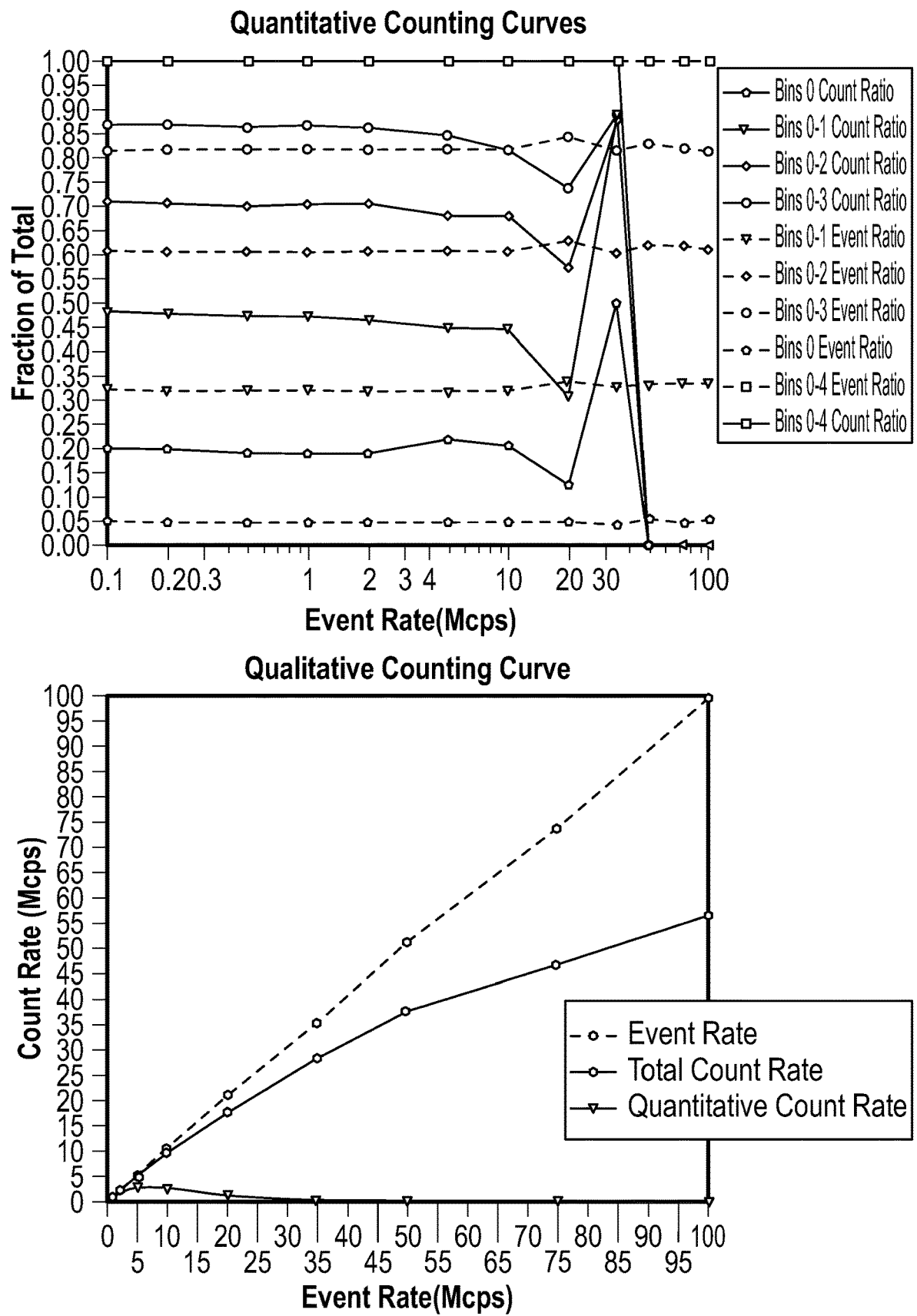

FIG. 6C illustrates counting of an event 620 detected at a POI in accordance with features of embodiments described herein for implementing a QPS counting method. As shown in FIG. 6C, the event 620 is not affected by charge sharing (no activity on waveforms corresponding to orthogonal neighbor discriminator outputs); however, the event 620 is affected by pileup, as indicated by ToT for bin 4 being exceeded by $2x$ (waveform 622). As a result, the event 620 is counted $2x$ by the quantitative counter (represented by a waveform 624).

FIGS. 7A-7D illustrate quantitative counting curves and qualitative counting curves for a variety of PCCT counting methods, including tickdown (FIG. 7A), QPS (FIG. 7B), tickdown with ToT (FIG. 7C), and QPS with ToT (FIG. 7D), as compared to ground truth. Note that the QPS with ToT method significantly improves the correlation between estimated and actual total counts and the correlation between estimated and actual proportions of counts by bin.

Figure 8:
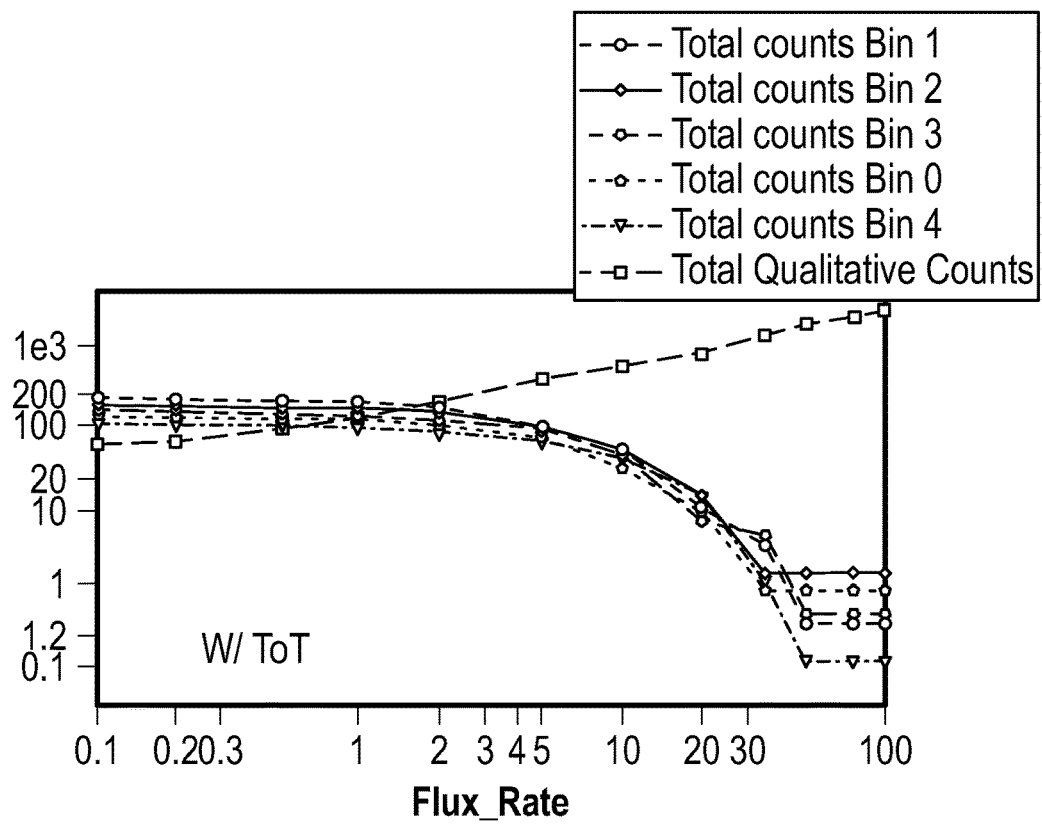
FIG. 8 illustrates total counting curves for QPS techniques with and without time-over-threshold (ToT) as compared to ground truth in accordance with features of embodiments described herein.
Figure 8:
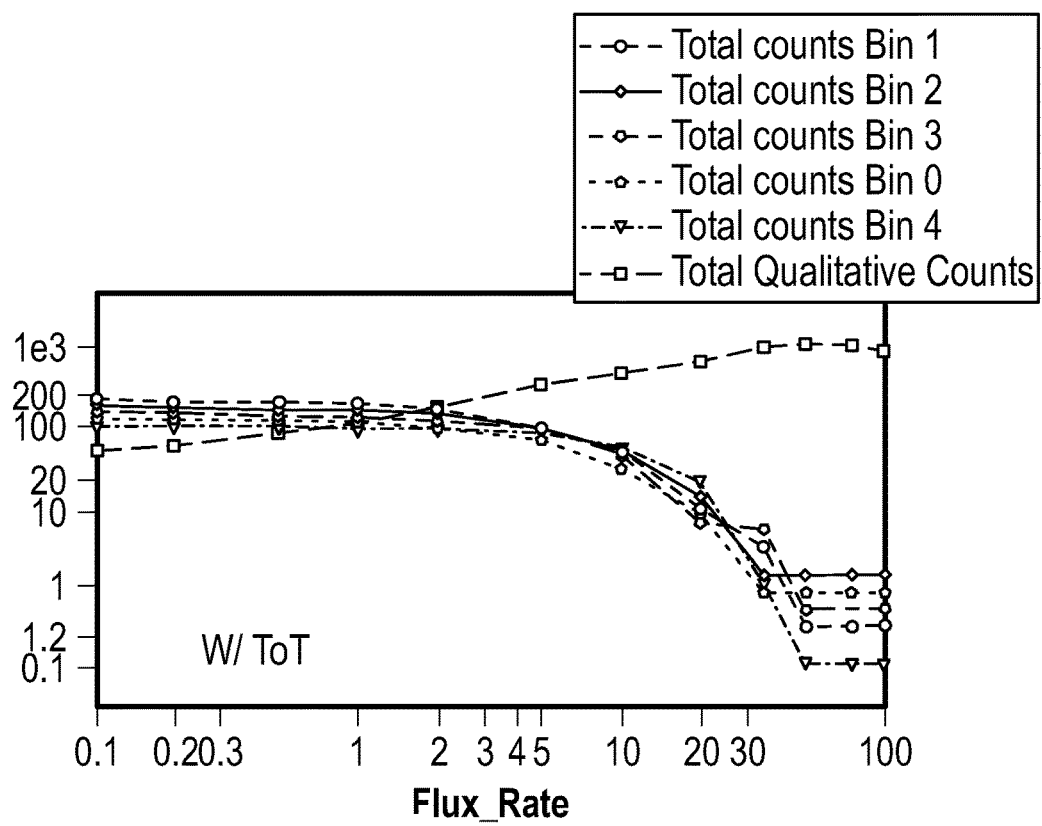

FIG. 8 illustrates total counting curves for QPS with and without ToT for purposes of comparison. As the flux rate increases, the number of quantitative counts increases monotonically, while the number of qualitative counts decreases. Measurements at the high end of the flux range contain little to no spectral information. This is a useful feature of the QPS method, as a low proportion of qualitative counts with respect to total counts can be used to indicate that the signal contains no useful spectral information. In some embodiments it may be beneficial to disregard the measured spectrum based on such an indicator, rather than to provide a spectral estimation that is inaccurate.

Charge sharing causes a spectral shift, mainly due to high-energy photons from neighboring pixels that share a significant fraction of charge into the POI in lower bins. A QPS technique as described herein can identify some of these events, resulting in an improvement in the accuracy of the low-flux spectrum. Particular results will depend on the choice of discriminator thresholds. QPS largely prevents spectral shift due to pileup, in which high bin (e.g., Bin 4) counts grow at the expense of other (lower) bins. Above about 10 mega counts per second (Mcps), the number of quantitative counts is so small that the information can be disregarded. As a result, a system employing QPS techniques is able to detect a condition in which nearly every charge event of a measurement frame is affected by either charge sharing or pileup, and thus the spectral information of the frame is highly corrupted and effectively useless. In other systems, the corrupt spectral information may be used to incorrectly present an inaccurate result as reliable.

The end goal of a CT scan is to produce a 3D image of the subject in which different materials can be identified. As such, one way to benchmark a PCCT counting method is to use it to perform a material identification task. For example, the counting data from a single pixel can be used to estimate the proportion of different materials present along a simulated linear x-ray photon trajectory.

Figure 9A:
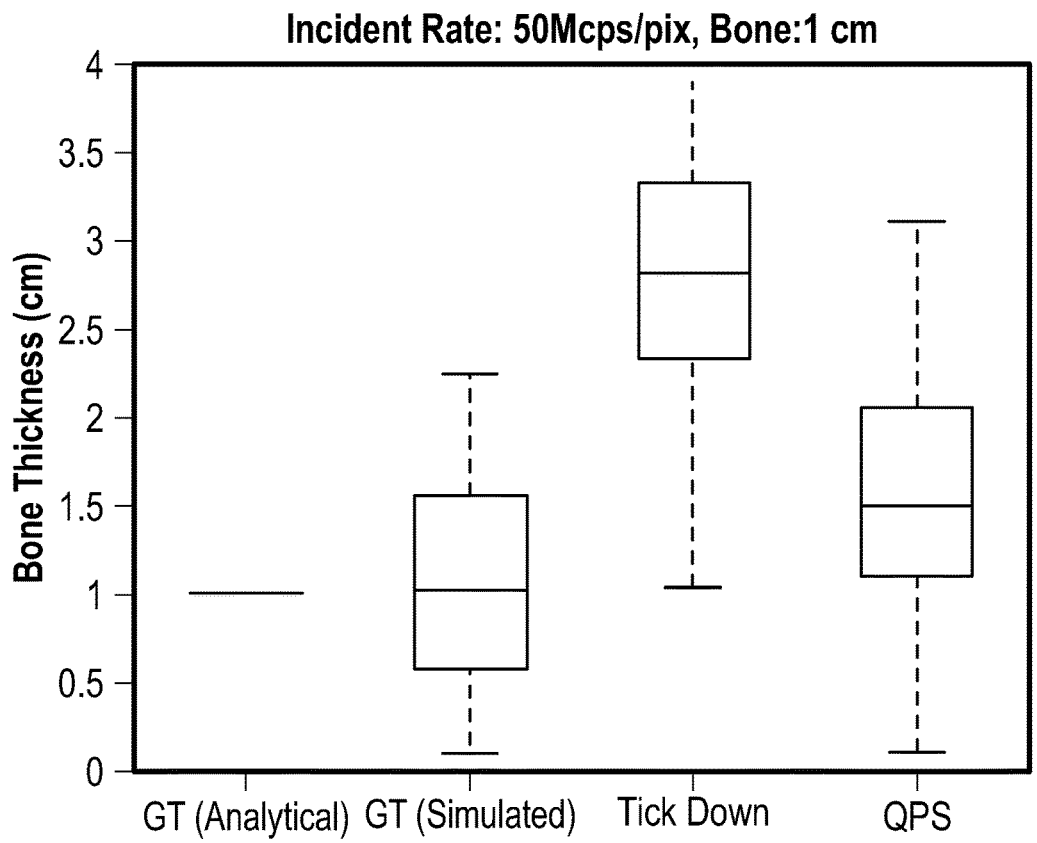
FIGS. 9A and 9B illustrate a series of estimations of the thickness of bone in a simulated data set in accordance with features of embodiments described herein.
Figure 9B:
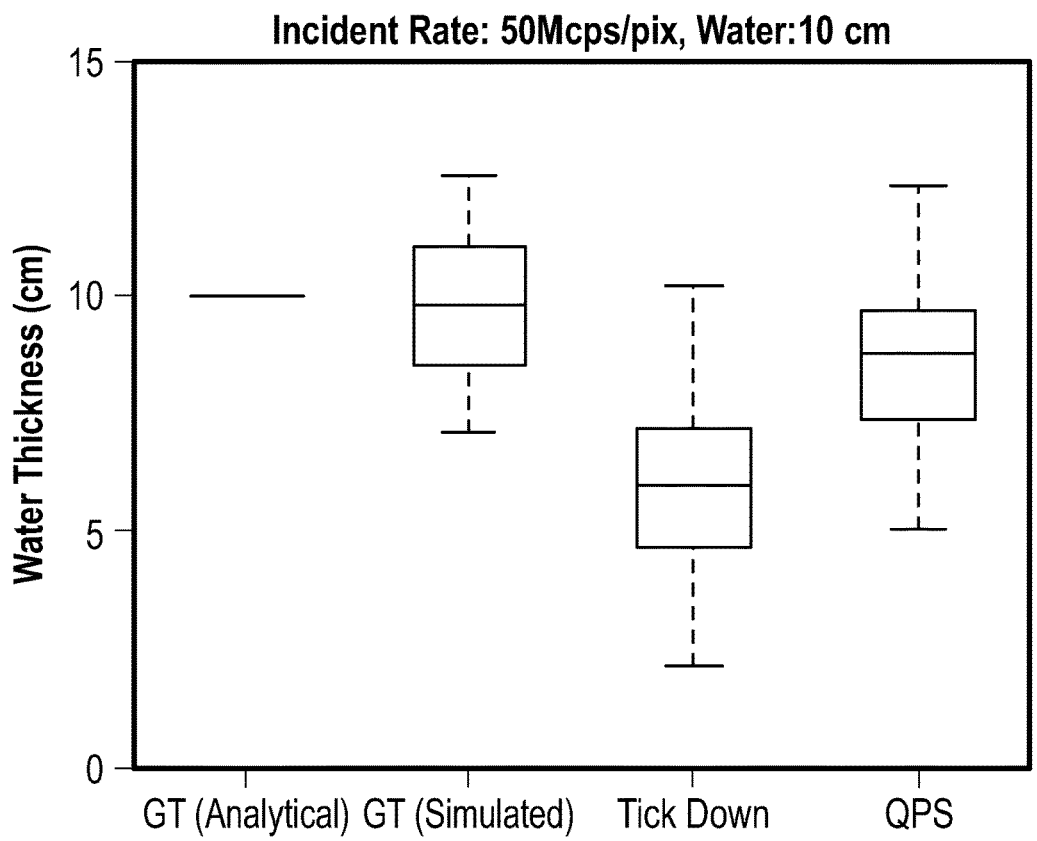

FIGS. 9A and 9B show the results of such a material identification experiment in which the simulated data corresponds to an X-ray beam passing through 10 cm of water (similar x-ray absorption to human tissue) and 1 cm of bone. Water and bone have different x-ray absorption characteristics, so the received photon counts can be used to estimate the proportion of water and bone along the simulated trajectory.

FIG. 9A represents a series of estimations of the thickness of bone in the simulated data set. In FIG. 9A, the first column labeled "GT (analytical)" shows the actual thickness of bone used to generate the simulated data. The other columns represent estimations of this bone thickness based on a series of Monte Carlo simulations using 3 different hypothetical photon counters. The second column labeled "GT (simulated)" represents the estimation based on an ideal photon counter-one that obtains the correct energy from each photon event, uncorrupted by pileup and charge sharing. The errors in this estimation are caused by the limited sample size of photons reaching the detector within a finite time frame. The third column labeled "Tick down" shows the estimation based on a simulated photon counter using the "tickdown" method. The fourth column labeled "QPS" represents an estimation based on a simulated photon counter using the QPS method.

FIG. 9B shows the results of the same experiment when the thickness of water in the simulated dataset is estimated.

The results of the experiment in FIGS. 9A and 9B show that the QPS method performs the material identification task with better accuracy than the tickdown method.

Figure 10:
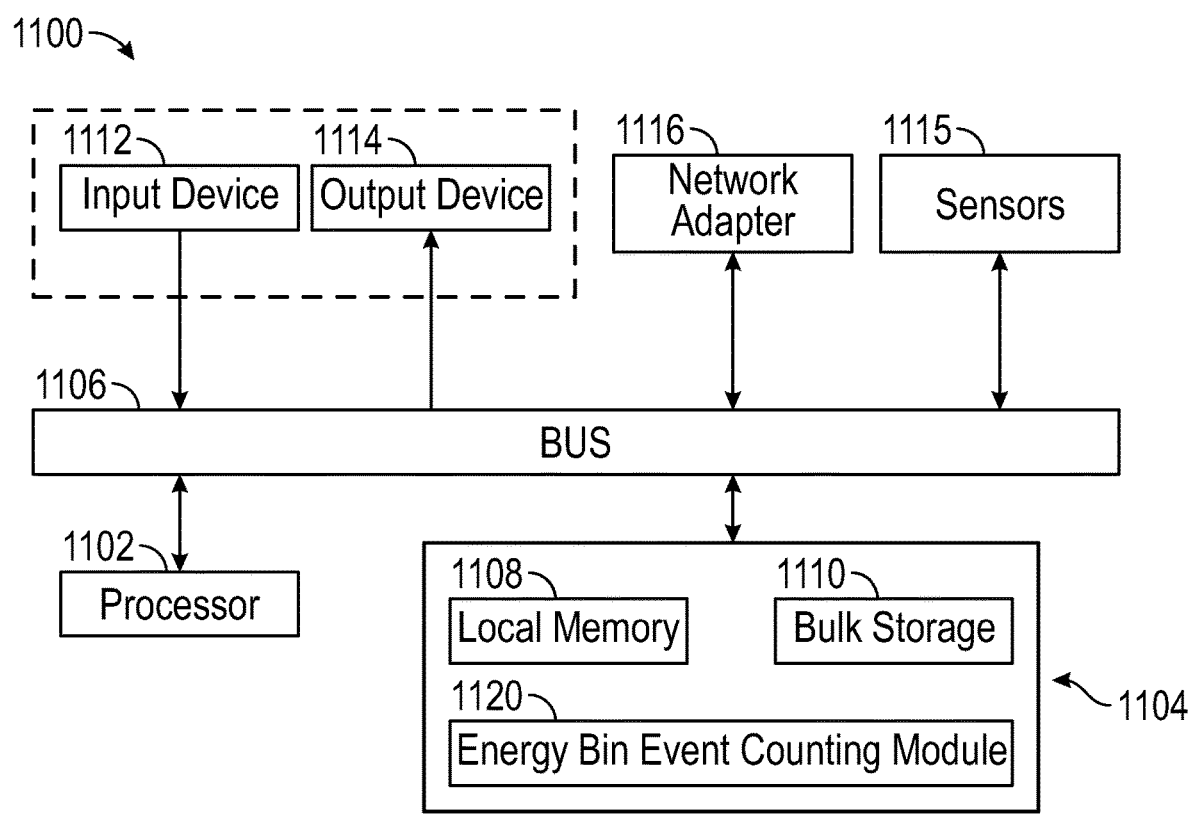
FIG. 10 is a block diagram of a computer system that may be used to implement all or some portion of a PCCT scanning system in accordance with features of certain embodiments described herein.

FIG. 10 is a block diagram illustrating an example system 1100 that may be configured to implement at least portions of techniques in accordance with embodiments described herein, and more particularly as shown in the FIGURES described hereinabove. As shown in FIG. 10, the system 1100 may include at least one processor 1102, e.g., a hardware processor 1102, coupled to memory elements 1104 through a system bus 1106. As such, the system may store program code and/or data within memory elements 1104. Further, the processor 1102 may execute the program code accessed from the memory elements 1104 via a system bus 1106. In one aspect, the system may be implemented as a computer that is suitable for storing and/or executing program code. It should be appreciated, however, that the system 1100 may be implemented in the form of any system including a processor and a memory that is capable of performing the functions described in this disclosure.

in some embodiments, the processor 1102 can execute software or an algorithm to perform the activities as discussed in this specification; in particular, activities related to embodiments described herein. The processor 1102 may include any combination of hardware, software, or firmware providing programmable logic, including by way of non-limiting example a microprocessor, a DSP, a field-programmable gate array (FPGA), a programmable logic array (PLA), an integrated circuit (IC), an application specific IC (ASIC), or a virtual machine processor. The processor 1102 may be communicatively coupled to the memory element 1104, for example in a direct-memory access (DMA) configuration, so that the processor 1102 may read from or write to the memory elements 1104.

In general, the memory elements 1104 may include any suitable volatile or non-volatile memory technology, including double data rate (DDR) random access memory (RAM), synchronous RAM (SRAM), dynamic RAM (DRAM), flash, read-only memory (ROM), optical media, virtual memory regions, magnetic or tape memory, or any other suitable technology. Unless specified otherwise, any of the memory elements discussed herein should be construed as being encompassed within the broad term "memory." The information being measured, processed, tracked or sent to or from any of the components of the system 1100 could be provided in any database, register, control list, cache, or storage structure, all of which can be referenced at any suitable timeframe. Any such storage options may be included within the broad term "memory" as used herein. Similarly, any of the potential processing elements, modules, and machines described herein should be construed as being encompassed within the broad term "processor." Each of the elements shown in the present figures may also include suitable interfaces for receiving, transmitting, and/or otherwise communicating data or information in a network environment so that they can communicate with, for example, a system having hardware similar or identical to another one of these elements.

In certain example implementations, mechanisms for implementing embodiments as outlined herein may be implemented by logic encoded in one or more tangible media, which may be inclusive of non-transitory media, e.g., embedded logic provided in an ASIC, in DSP instructions, software (potentially inclusive of object code and source code) to be executed by a processor, or other similar machine, etc. In some of these instances, memory elements, such as e.g., the memory elements 1104 shown in FIG. 10 can store data or information used for the operations described herein. This includes the memory elements being able to store software, logic, code, or processor instructions that are executed to carry out the activities described herein. A processor can execute any type of instructions associated with the data or information to achieve the operations detailed herein. In one example, the processors, such as e.g., the processor 1102 shown in FIG. 10, could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., an FPGA, a DSP, an erasable programmable read-only memory (EPROM), an electrically erasable programmable read-only memory (EEPROM)) or an ASIC that includes digital logic, software, code, electronic instructions, or any suitable combination thereof.

The memory elements 1104 may include one or more physical memory devices such as, for example, local memory 1108 and one or more bulk storage devices 1110. The local memory may refer to RAM or other non-persistent memory device(s) generally used during actual execution of the program code. A bulk storage device may be implemented as a hard drive or other persistent data storage device. The processing system 1100 may also include one or more cache memories (not shown) that provide temporary storage of at least some program code in order to reduce the number of times program code must be retrieved from the bulk storage device 1110 during execution.

As shown in FIG. 10, the memory elements 1104 may store an energy bin event counting module 1120. In various embodiments, the module 1120 may be stored in the local memory 1108, the one or more bulk storage devices 1110, or apart from the local memory and the bulk storage devices. It should be appreciated that the system 1100 may further execute an operating system (not shown in FIG. 10) that can facilitate execution of the module 1120. The module 1120, being implemented in the form of executable program code and/or data, can be read from, written to, and/or executed by the system 1100, e.g., by the processor 1102. Responsive to reading from, writing to, and/or executing the module 1120, the system 1100 may be configured to perform one or more operations or method steps described herein.

Input/output (I/O) devices depicted as an input device 1112 and an output device 1114, optionally, may be coupled to the system. Examples of input devices may include, but are not limited to, a keyboard, a pointing device such as a mouse, or the like. Examples of output devices may include, but are not limited to, a monitor or a display, speakers, or the like. In some implementations, the system may include a device driver (not shown) for the output device 1114. Input and/or output devices 1112, 1114 may be coupled to the system 1100 either directly or through intervening I/O controllers. Additionally, sensors 1115, may be coupled to the system 1100 either directly or through intervening controllers and/or drivers.

In an embodiment, the input and the output devices may be implemented as a combined input/output device (illustrated in FIG. 10 with a dashed line surrounding the input device 1112 and the output device 1114). An example of such a combined device is a touch sensitive display, also sometimes referred to as a "touch screen display" or simply "touch screen". In such an embodiment, input to the device may be provided by a movement of a physical object, such as, e.g., a stylus or a finger of a user, on or near the touch screen display.

A network adapter 1116 may also, optionally, be coupled to the system 1100 to enable it to become coupled to other systems, computer systems, remote network devices, and/or remote storage devices through intervening private or public networks. The network adapter may comprise a data receiver for receiving data that is transmitted by said systems, devices and/or networks to the system 1100, and a data transmitter for transmitting data from the system 1100 to said systems, devices and/or networks. Modems, cable modems, and Ethernet cards are examples of different types of network adapter that may be used with the system 1100.

Example 1 provides a method for counting charge events detected by a pixel in a photon-counting computed tomography (PCCT) scanning system including a plurality of discriminators, in which each discriminator is associated with a respective one of a plurality of threshold voltage levels, the method including detecting a signal output from one of the discriminators; incrementing a quantitative count corresponding to the threshold voltage level associated with the one of the discriminators if the detected discriminator output signal meets a first condition; and incrementing a qualitative count if the detected discriminator output signal meets at least one second condition.

Example 2 provides the method of example 1, in which the at least one second condition includes expiration of a time-over-threshold (ToT) timer.

Example 3 provides the method of example 2, further including, upon expiration of the ToT timer, incrementing the qualitative count and resetting the ToT timer.

Example 4 provides the method of example 1, in which the at least one second condition includes the signal output from the one of the discriminators overlapping with a signal output from a discriminator associated with a neighboring pixel.

Example 5 provides the method of example 1, in which the at least one second condition includes the signal output from the one of the discriminators including only one monotonic series of low-to-high transition and only one monotonic series of high-to-low transition.

Example 6 provides the method of example 1, in which the first condition includes an absence of the at least one second condition.

Example 7 provides the method of example 1, in which the plurality of discriminators includes five discriminators.

Example 8 provides the method of example 1, in which the plurality of threshold voltage levels include five threshold voltage levels.

Example 9 provides the method of example 1, in which each of the discriminators compares a voltage signal input to the discriminators to the threshold voltage level associated with the discriminator.

Example 10 provides the method of example 9, in which an output of each of the discriminators is driven high when the voltage signal input to the discriminators exceeds the threshold voltage level associated with the discriminator.

Example 11 provides the method of example 1, in which the spectral information is disregarded if a certain threshold for total number of qualitative counts is not reached.

Example 12 provides a method for counting charge events detected by a pixel in a photon-counting computed tomography (PCCT) scanning system including a plurality of discriminators, in which each discriminator is associated with a respective one of a plurality of threshold voltage levels, the method including detecting a signal output from one of the discriminators; and incrementing a qualitative count upon the occurrence of at least one of expiration of a time-over-threshold (ToT) timer, the signal output from the one of the discriminators overlapping with a signal output from a discriminator associated with a neighboring pixel, and the signal output from the one of the discriminators including only one monotonic low-to-high transitions and monotonic high-to-low transitions; otherwise, incrementing a quantitative count corresponding to the threshold voltage level associated with the one of the discriminators.

Example 13 provides the method of example 12, further including, upon expiration of the ToT timer incrementing the qualitative count and resetting the ToT timer.

Example 14 provides a photon-counting computed tomography (PCCT) scanning system including a plurality of discriminators, in which each discriminator is associated with a respective one of a plurality of threshold voltage levels and counting circuitry configured to detect a signal output from one of the discriminators; increment a quantitative count corresponding to the threshold voltage level associated with the one of the discriminators if the detected discriminator output signal meets a first condition; and increment a qualitative count if the detected discriminator output signal meets at least one second condition.

Example 15 provides the PCCT scanning system of example 14, in which the at least one second condition includes expiration of a time-over-threshold (ToT) timer.

Example 16 provides the PCCT system of example 15, further including, upon expiration of the ToT timer incrementing the qualitative count and resetting the ToT timer.

Example 17 provides the PCCT system of example 14, in which the at least one second condition includes the signal output from the one of the discriminators overlapping with a signal output from a discriminator associated with a neighboring pixel.

Example 18 provides the PCCT system of example 14, in which the at least one second condition includes the signal output from the one of the discriminators including only one monotonic series of low-to-high transitions and one monotonic series of high-to-low transitions.

Example 19 provides the PCCT system of example 14, in which the first condition includes an absence of the at least one second condition.

Example 20 provides the PCCT system of example 14, in which the plurality of discriminators includes five discriminators.

Example 21 provides the PCCT system of example 14, in which the plurality of threshold voltage levels include five threshold voltage levels.

Example 22 provides the PCCT system of example 14, in which each of the discriminators compares a voltage signal input to the discriminators to the threshold voltage level associated with the discriminator.

Example 23 provides the PCCT system of example 14, in which an output of each of the discriminators is driven high when the voltage signal input to the discriminators exceeds the threshold voltage level associated with the discriminator.

It should be noted that all of the specifications, dimensions, and relationships outlined herein (e.g., the number of elements, operations, steps, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, exemplary embodiments have been described with reference to particular component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system may be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and may accommodate a large number of components, as well as more complicated/sophisticated arrangements and configurations. Accordingly, the examples provided should not limit the scope or inhibit the broad teachings of the electrical circuits as potentially applied to myriad other architectures.

It should also be noted that in this Specification, references to various features (e.g., elements, structures, modules, components, steps, operations, characteristics, etc.) included in "one embodiment", "exemplary embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It should also be noted that the functions related to circuit architectures illustrate only some of the possible circuit architecture functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that all optional features of the device and system described above may also be implemented with respect to the method or process described herein and specifics in the examples may be used anywhere in one or more embodiments.

The 'means for' in these instances (above) may include (but is not limited to) using any suitable component discussed herein, along with any suitable software, circuitry, hub, computer code, logic, algorithms, hardware, controller, interface, link, bus, communication pathway, etc.

Note that with the example provided above, as well as numerous other examples provided herein, interaction may be described in terms of two, three, or four network elements. However, this has been done for purposes of clarity and example only. In certain cases, it may be easier to describe one or more of the functionalities of a given set of flows by only referencing a limited number of network elements. It should be appreciated that topologies illustrated in and described with reference to the accompanying FIGURES (and their teachings) are readily scalable and may accommodate a large number of components, as well as more complicated/sophisticated arrangements and configurations. Accordingly, the examples provided should not limit the scope or inhibit the broad teachings of the illustrated topologies as potentially applied to myriad other architectures.

It is also important to note that the steps in the preceding flow diagrams illustrate only some of the possible signaling scenarios and patterns that may be executed by, or within, communication systems shown in the FIGURES. Some of these steps may be deleted or removed where appropriate, or these steps may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by communication systems shown in the FIGURES in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. For example, although the present disclosure has been described with reference to particular communication exchanges, embodiments described herein may be applicable to other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 142 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method for counting charge events in a photon-counting computed tomography (PCCT) scanning system, the method comprising:
   detecting a signal output from a discriminator of a plurality of discriminators included in the PCCT scanning system, with the discriminator associated with a pixel in the PCCT scanning system, wherein each discriminator of the plurality of discriminators is associated with a respective one of a plurality of threshold voltage levels,
   incrementing a quantitative count corresponding to a threshold voltage level associated with the discriminators in response to the detected signal output satisfying a first condition; and
   incrementing a qualitative count in response to the detected signal output satisfying at least one second condition, with the qualitative count defining a number of pileup charge events charge-sharing charge events, or a combination thereof.

2. The method of claim 1, wherein the at least one second condition includes expiration of a time-over-threshold (ToT) timer.

3. The method of claim 2, further comprising, in response to expiration of the ToT timer:
   incrementing the qualitative count; and
   resetting the ToT timer.

4. The method of claim 1, wherein the at least one second condition includes the signal output overlapping with a second signal output from a discriminator associated with a neighboring pixel.

5. The method of claim 1, wherein the at least one second condition includes the signal output comprising a monotonic series of low-to-high transitions followed by a monotonic series of high-to-low transitions.

6. The method of claim 1, wherein the first condition comprises absence of the at least one second condition.

7. The method of claim 1, wherein the plurality of discriminators comprises five discriminators.

8. The method of claim 1, wherein the plurality of threshold voltage levels comprise five threshold voltage levels.

9. The method of claim 1, wherein a first discriminator of the plurality of discriminators compares a voltage signal input to the plurality of discriminators to a threshold voltage level associated with the first discriminator.

10. The method of claim 9, wherein an output of the first discriminator of the plurality of discriminators is driven high when the voltage signal input to the plurality of discriminators exceeds the threshold voltage level.

11. The method of claim 1, wherein spectral information is disregarded in response to a threshold number for total number of qualitative counts is not reached.

12. A method for counting charge events in a photon-counting computed tomography (PCCT) scanning system, the method comprising:
   detecting a signal output from a discriminator of a plurality of discriminators included in the PCCT scanning system, with the discriminator associated with a pixel in the PCCT scanning system, wherein each discriminator of the plurality of discriminators is associated with a respective one of a plurality of threshold voltage levels; and incrementing a qualitative count in response to occurrence of at least one of:
- a first condition defined by expiration of a time-over-threshold (ToT) timer;
- a second condition defined by the signal output overlapping with a second signal output from a discriminator associated with a neighboring pixel; or
- a third condition defined by the signal output comprising a monotonic series of low-to-high transitions starting at a baseline level followed by a monotonic series of high-to-low transitions terminating at the baseline level; and in absence of occurrence the first condition, the second condition, or the third condition, incrementing a quantitative count corresponding to a threshold voltage level associated with the discriminator.

13. The method of claim 12, further comprising, in response to expiration of the ToT timer;
resetting the ToT timer.

14. A photon-counting computed tomography (PCCT) scanning system comprising:
a plurality of discriminators, wherein each discriminator is associated with a respective one of a plurality of threshold voltage levels; and
counting circuitry configured to:
- detect a signal output from a discriminator of the plurality of discriminators; and
- increment a quantitative count corresponding to a threshold voltage level associated with the discriminator in response to the detected signal output satisfying a first condition; and
- increment a qualitative count in response to the detected signal output satisfying at least one second condition, with the qualitative count defining a number of pileup charge events, charge-sharing charge events, or a combination thereof.

15. The PCCT scanning system of claim 14, wherein the at least one second condition includes expiration of a time-over-threshold (ToT) timer.

16. The PCCT scanning system of claim 15, wherein in response to expiration of the ToT timer, the counting circuitry is further configured to:
increment the qualitative count; and
reset the ToT timer.

17. The PCCT scanning system of claim 14, wherein the at least one second condition includes the signal output overlapping with a second signal output from a discriminator associated with a neighboring pixel.

18. The PCCT scanning system of claim 14, wherein the at least one second condition includes the signal output comprising a monotonic series of low-to-high transitions followed by a monotonic series of high-to-low transitions.

19. The PCCT scanning system of claim 14, wherein the first condition comprises absence of the at least one second condition.

20. The PCCT scanning system of claim 14, wherein a first discriminator of the plurality of discriminators compares a voltage signal input to the discriminators to a threshold voltage level associated with the first discriminator, and wherein an output of the first discriminator is driven high in response to the voltage signal input to the discriminators exceeding the threshold voltage level.

* * * * *